United States Patent [19]
Cragoe, Jr. et al.

[11] 3,966,966
[45] June 29, 1976

[54] PHARMACEUTICAL COMPOSITIONS AND METHOD OF TREATMENT EMPLOYING 1,3-DIOXO-2,2-DISUBSTITUTED INDANYLOXY ALKANOIC ACIDS

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[22] Filed: July 31, 1974

[21] Appl. No.: 492,942

Related U.S. Application Data

[63] Continuation-in-part of Ser. No. 405,967, Oct. 12, 1973.

[52] U.S. Cl. .......................... 424/317; 260/308 D; 424/275
[51] Int. Cl.² ........................................ A61K 31/19
[58] Field of Search ..................... 424/317; 405/967

[56] References Cited
UNITED STATES PATENTS
3,704,314  11/1972  Cragoe, Jr. .......................... 260/520

*Primary Examiner*—Frederick E. Waddell
*Attorney, Agent, or Firm*—Michael C. Sudol, Jr.; J. Jerome Behan

[57] ABSTRACT

[1,3-Dioxo-2-substituted and 2,2-disubstituted-indanyloxy(or thio)]alkanoic acids and their salts, esters and amides are disclosed. The products display a dual pharmaceutical utility in that they exhibit diuretic, saluretic and uricosuric activity. The acid products are prepared by treating a (2- or 2,2-di)substituted-6-hydroxy-(or mercapto)-1,3-indanedione with a haloalkanoic acid or ester thereof and if the ester is employed hydrolyzing the ester.

4 Claims, No Drawings

PHARMACEUTICAL COMPOSITIONS AND METHOD OF TREATMENT EMPLOYING 1,3-DIOXO-2,2-DISUBSTITUTED INDANYLOXY ALKANOIC ACIDS

This application is a continuation-in-part of our copending application Ser. No. 405,967 filed Oct. 12, 1973.

This invention relates to a new class of chemical compounds which can be described generally as [1,3-dioxo-2-substituted and 2,2-disubstituted-indanyloxy-(or thio)]alkanoic acids and to the non-toxic, pharmacologically acceptable salt, ester and amide derivatives. It is also an object of this invention to describe a method for the preparation of the [1,3-dioxo-2-substituted and 2,2-disubstituted-indanyloxy(or thio)]alkanoic acids. Pharmacological studies show that the instant products are effective diuretic and saluretic agents which can be used in the treatment of conditions associated with electrolyte and fluid retention. The instant products are also useful in the treatment of hypertension. In addition, these compounds are able to maintain the uric acid concentration in the body at pretreatment levels or to even effect a decrease in the uric acid concentration.

When administered in therapeutic dosages, in conventional vehicles, the instant products effectively reduce the amount of sodium and chloride ions in the body, lower dangerous excesses of fluid levels to acceptable levels and, in general, alleviate conditions usually associated with edema. In addition, these compounds overcome a major problem associated with many of the presently available diuretics and saluretics. Many of the presently available diuretics and saluretics have a tendency upon administration to induce hyperuricemia which may precipitate uric acid or sodium urate, or both, in the body which may cause from mild to severe cases of gout. The instant compounds of this invention now provide an effective tool to treat those patients requiring diuretic and saluretic treatment without incurring the risk of inducing gout.

[1,3-Dioxo-2-substituted and 2,2-disubstituted-indanyloxy(or thio)]alkanoic acids of the invention include the racemates and pure enantiomers which have the following structural formula:

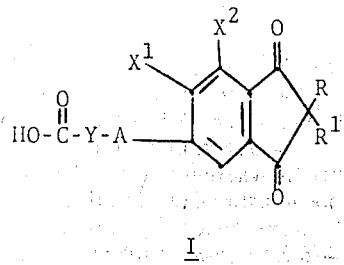

I wherein

A is oxygen or sulfur;

R is lower alkyl containing from 1 to 5 carbon atoms such as methyl, ethyl, n-propyl, isopropyl, n-butyl, isobutyl, tert-butyl, n-pentyl and the like; cycloalkyl, for example, cycloalkyl containing from 5–6 nuclear carbon atoms such as cyclopentyl, cyclohexyl and the like, aryl such as phenyl and substituted aryl wherein the substituent is lower alkyl or halo; thienyl and substituted thienyl wherein the substituent is lower alkyl or halo;

$R^1$ is hydrogen, lower alkyl containing from 1 to 5 carbon atoms such as methyl, ethyl, n-propyl, isopropyl, n-butyl, isobutyl, tert-butyl, n-pentyl and the like, lower alkenyl containing from 3 to 5 carbon atoms such as allyl, 1-, 2- or 3-butenyl, 1-, 2-, 3- or 4-pentenyl and the like, lower alkynyl containing from 3 to 5 carbon atoms such as propargyl, 1-, 2- or 3-butynyl, 1-, 2-, 3- or 4-pentynyl and the like, phenyl lower alkyl wherein the lower alkyl contains from 1 to 3 carbon atoms such as benzyl, phenethyl, phenylpropyl and the like, phenyl lower alkenyl wherein the lower alkenyl contains from 2–5 carbon atoms such as cinnamyl and the like, aryl such as phenyl or substituted aryl such as loweralkylaryl or haloaryl; thienyl or substituted thienyl such as lower alkylthienyl or halothienyl, or R and $R^1$ may be joined together with the carbon atoms to which they are attached to form a cycloalkyl radical containing from 3 to 7 nuclear carbon atoms, for example, cyclopropyl, cyclobutyl, cyclopentyl, cyclohexyl, cycloheptyl and the like;

$X^1$ is hydrogen, methyl or halo such as chloro, bromo, fluoro and the like; and $X^2$ is methyl or halo such as chloro, bromo, fluoro and the like or $X^1$ and $X^2$ may be joined to form a hydrocarbylene chain containing from 3 to 4 carbon atoms, for example, trimethylene, tetramethylene, 1,3-butadienylene and the like, and Y is an alkylene or haloalkylene radical having a maximum of 4 carbon atoms which contain from 1–3 linear carbon atoms between the oxy (or thio) and carboxy group, for example, methylene, ethylidene, propylidene, isopropylidene, ethylene, trimethylene, fluoromethylene and the like, and the non-toxic pharmaceutically acceptable salt, ester and amide derivatives thereof.

The preferred embodiments of this invention are the racemates and the pure enantiomers of [1,3-dioxo-2-substituted and 2,2-disubstituted-indanyloxy(or thio)-]alkanoic acids having the following structural formula:

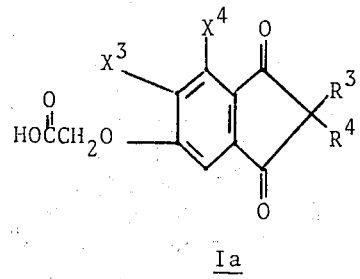

Ia wherein $R^3$ is lower alkyl containing from 1 to 3 carbon atoms such as methyl, ethyl, n-propyl or isopropyl or cycloalkyl containing 5 or 6 nuclear carbon atoms such as cyclopentyl or cyclohexyl and $R^4$ is hydrogen, lower alkyl containing from 1 to 3 carbon atoms such as methyl, ethyl, n-propyl or isopropyl, phenyl, lower alkylphenyl wherein the lower alkyl contains from 1 to 3 carbon atoms such as methyl, ethyl, n-propyl or isopropyl, halophenyl, thienyl, lower alkyl thienyl wherein the lower alkyl contains from 1 to 3 carbon atoms such as methyl, ethyl, n-propyl or isopropyl, halothienyl; or $R^3$ and $R^4$ may be joined together with the carbon atom to which they are attached to form a cycloalkyl radical containing from 5 to 6 nuclear carbon atoms such as cyclopentyl, cyclohexyl and the like, and $X^3$ and $X^4$ are the same or different radicals selected from methyl or chloro; and the non-toxic, pharmacologically acceptable salt, ester and amide derivatives.

The foregoing class of compounds exhibits particularly good diuretic and saluretic activity and also either maintains the uric acid concentration in the body at pretreatment levels or even causes a decrease in the uric acic concentration.

A further more preferred embodiment of this invention are the racemates and pure enantiomers of [1,3-dioxo-2-substituted and 2,2-disubstituted-indanyloxy-(or thio)]alkanoic acids having the formula:

The foregoing especially preferred class of compounds also exhibit particularly good diuretic and saluretic activity and also either maintain the uric acid concentration in the body at pretreatment levels or even cause a decrease in the uric acid concentration.

The [1,3-dioxo-2-substituted and 2,2-disubstituted-indanyloxy(or thio)]alkanoic acids and ester (I) wherein Y contains 1 or 3 linear carbon atoms may be prepared by an etherification method which comprises reacting a haloalkanoic acid or ester thereof of the formula:

wherein
$R^5$ is hydrogen or lower alkyl such as methyl, ethyl and the like, and
Z is halo such as bromo, chloro, iodo and the like with a suitable 2-mono or 2,2-disubstituted-6-hydroxy (or mercapto)-1,3-indanedione (II, infra).
The following equation illustrates this reaction:

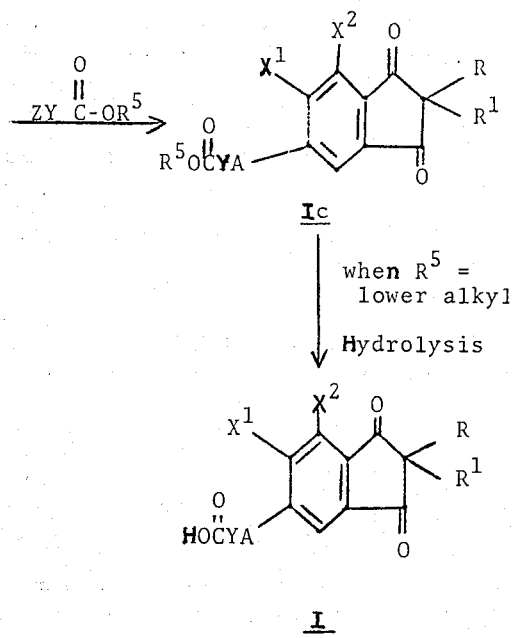

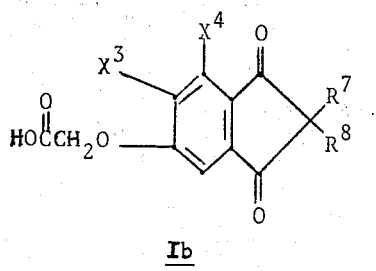

Ib wherein
$R^7$ is lower alkyl containing 1 to 3 carbon atoms such as methyl, ethyl, n-propyl or isopropyl;
$R^8$ is hydrogen, lower alkyl containing from 1 to 3 carbon atoms such as methyl, ethyl, n-propyl, isopropyl, phenyl, p-chlorophenyl or thienyl; and
$X^3$ and $X^4$ are the same or different radicals selected from methyl or chloro; and the non-toxic pharmaceutically acceptable salt and ester derivatives thereof.

wherein $X^1$, $X^2$, R, $R^5$ and Z are as defined above;
$R^1$ is lower alkyl, lower alkenyl, halo lower alkenyl, lower alkynyl, phenyl lower alkyl, phenyl lower alkenyl, aryl or substituted aryl, thienyl or substituted thienyl, wherein these substituents are as defined above under the definition of $R^1$; or
R and $R^1$ may be joined together with the carbon atom to which they are attached to form a cycloalkyl radical containing from 4 to 7 nuclear carbon atoms; and
Y is an alkylene or haloalkylene radical containing 1 or 3 linear carbon atoms as defined above.

In general, the reaction is conducted in the presence of a base such as an alkali metal carbonate, hydroxide or alkoxide such as potassium carbonate, sodium carbonate, potassium hydroxide, sodium hydroxide, sodium ethoxide and the like. Any solvent which is inert or substantially inert to the reactants and in which the reagents are reasonably soluble may be employed. Acetone, ethanol and dimethylformamide, for example, have proved to be particularly advantageous solvents. The reaction may be conducted at a temperature in the range of from about 25°C. to the reflux temperature of the particular solvent employed. The reaction with the haloalkanoic acid or ester is generally complete in about 10 to 60 minutes. If the haloalkanoic acid ester is employed, the ester obtained may be hydrolyzed to the free acid by methods well known to those skilled in the art.

Those [1,3-dioxo-2-substituted and 2,2-disubstituted-indanyloxy(or thio)]alkanoic acids (I) wherein the alkylene chain contains 2 linear carbon atoms between the carboxy and oxy (or thio) groups are prepared from their corresponding 2-mono or 2,2-disubstituted-6-hydroxy-(or mercapto)-1,3-indanediones (II) by the reaction of the latter with propiolactone or with an appropriately substituted propiolactone, in the presence of a base such as an aqueous solution of sodium hydroxide, preferably, while heating the solution at reflux temperatures; followed by the acidification of the carboxylate intermediate thus formed to the desired acid. The following equation illustrates the reaction:

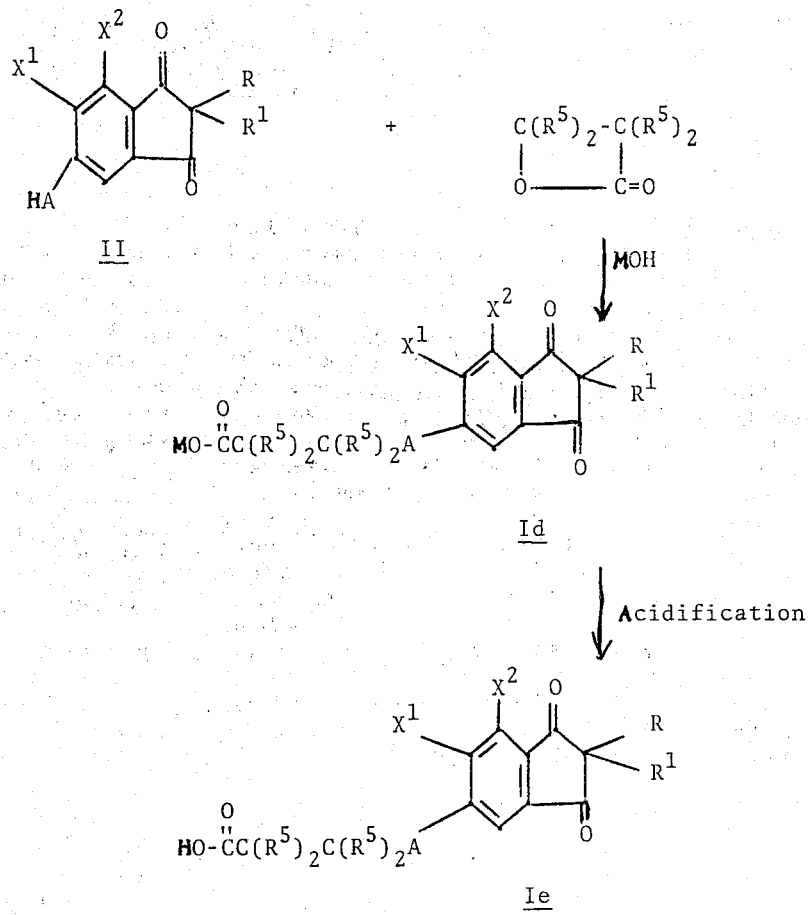

wherein A, R, $R^1$, $R^5$, $X^1$ and $X^2$ are as defined above and M is a cation derived from an alkali metal hydroxide or alkali metal carbonate such as sodium or potassium cation.

Another process for preparing [1,3-dioxo-2-substituted and 2,2-disubstituted-indanyloxy(or thio)]alkanoic acids comprises reacting a substituted phenoxyalkanoic acid, a substituted phenylthioalkanoic acid or a lower alkyl ester of the acid with a mono- or di-substituted malonyl chloride in the presence of a Friedel Crafts catalyst such as aluminum chloride and the like. The reaction solvent and the temperature at which the reaction is conducted are not particularly critical aspects of this reaction inasmuch as any solvent which is inert to the starting materials may be employed with good results. In this regard, it has been found that methylene chloride is a particularly suitable solvent. The following equation illustrates this reaction:

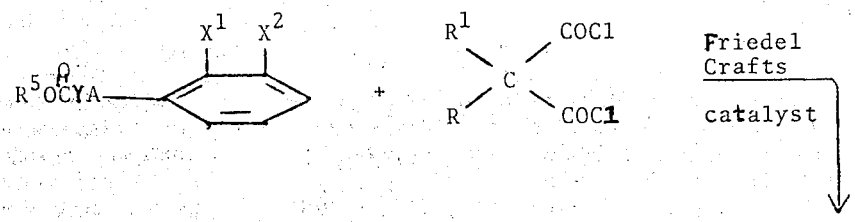

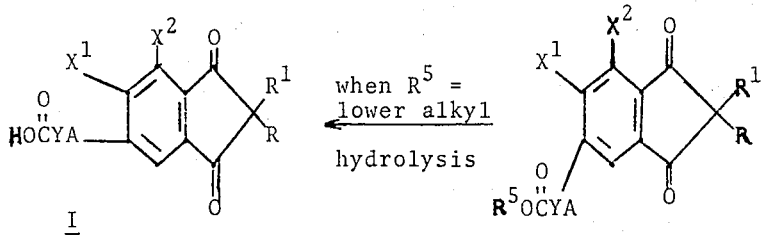

wherein $X^1$, $X^2$, A, Y and $R^5$ are as previously defined and wherein R and $R^1$ are as previously defined with the exception that R and $R^1$ are not aryl, substituted aryl, thienyl and substituted thienyl.

It should be noted that if a lower alkyl ester of a substituted phenoxyalkanoic acid or a substituted phenylthio alkanoic acid is used, the ester obtained (Ic) may be hydrolyzed to the free acid by methods well known to those skilled in the art.

The 2-mono- or 2,2-disubstituted-6-hydroxy-(or mercapto)-1,3-indanediones (II, infra), which also exhibit diuretic and uricosuric activity, are prepared by treating the correspondingly substituted 2-substituted-6-lower alkoxy-(or lower alkylthio)-1,3-indanedione with an ether cleaving reagent such as aluminum chloride, pyridine hydrochloride, sodium in liquid ammonia and the like. When aluminum chloride is employed, the solvent may be heptane, carbon disulfide, methylene chloride and the like and when pyridine hydrochloride is employed, it is not necessary to employ a solvent. The following equation illustrates this process:

of a 2,3-disubstituted phenol (or thiophenol) Compound IV (known compounds) is reacted with a mono- or di-substituted malonyl chloride in the presence of a Friedel Crafts catalyst such as aluminum chloride and the like. The reaction solvent and the temperature at which the reaction is conducted are not particularly critical aspects of this invention inasmuch as any solvent which is inert to the reactants may be employed with good results. In this regard, methylene chloride has been found to be a particularly good solvent.

Another method for preparing a 2,2-disubstituted-6-lower alkoxy-1,3-indanedione (IIIa, infra) consists of alkylating or arylating a 2-monosubstituted-6-lower alkoxy-1,3-indanedione (V, infra) with an alkylating agent $R^2Z$ wherein $R^2$ is lower alkyl containing from 1 to 5 carbon atoms such as methyl, ethyl, n-propyl, isopropyl, n-butyl, isobutyl, tert-butyl, n-pentyl and the like, lower alkenyl containing from 3 to 5 carbon atoms such as allyl, 1-, 2- or 3-butenyl, 1-, 2-, 3- or 4-pentenyl

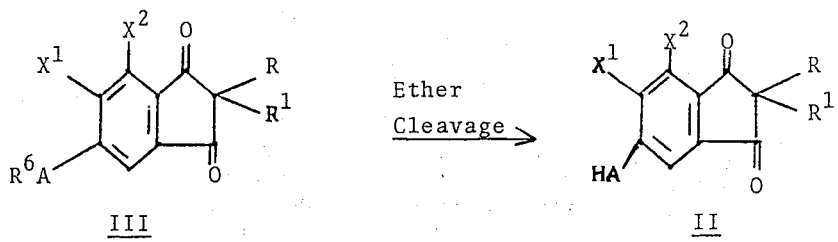

wherein A, R, $R^1$, $X^1$ and $X^2$ are as defined above, and $R^6$ is lower alkyl.

Compounds shown as III above can be prepared by several methods. The following equation illustrates one process:

and the like, lower alkynyl containing from 3 to 5 carbon atoms such as propargyl, 1-, 2- or 3-butynyl, 1-, 2-, 3- or 4-pentynyl and the like, phenyl lower alkyl wherein the lower alkyl contains from 1 to 3 carbon atoms such as benzyl, phenethyl,

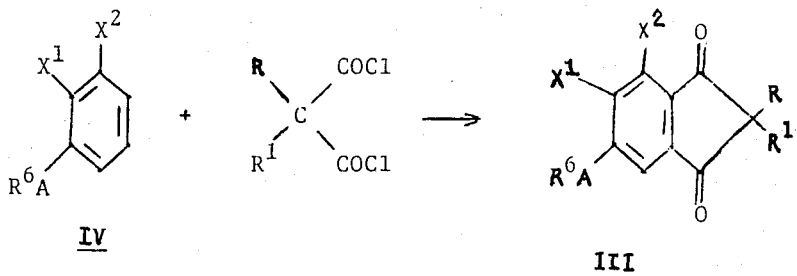

wherein $X^1$, $X^2$, $R^6$ and A are as described above and wherein R and $R^1$ are as previously defined with the exception that R and $R^1$ are not aryl, substituted aryl, thienyl and substituted thienyl.

Generally to prepare Compound III above, an ether phenylpropyl and the like, phenyl lower alkenyl wherein the lower alkenyl contains from 2 to 5 carbon atoms such as cinnamyl and the like, and R, $R^6$, $X^1$, $X^2$ and Z are as defined above.

The following equation illustrates this process:

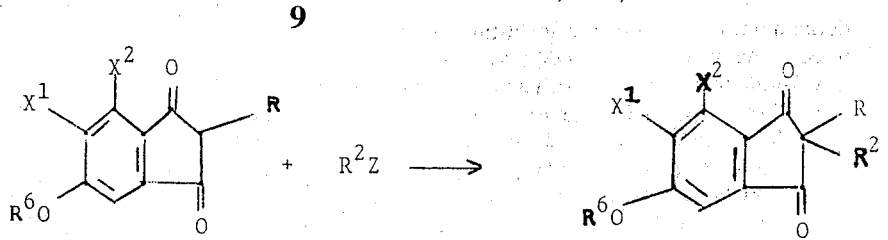

In general, the reaction is conducted in the presence of a base such as an alkali metal carbonate, hydroxide or alkoxide such as potassium carbonate, sodium carbonate, potassium hydroxide, sodium hydroxide, sodium ethoxide and the like. Any solvent which is inert or substantially inert to the reactants and in which the reagents are reasonably soluble may be employed. Acetone, ethanol and dimethylformamide, for example, have proved to be particularly advantageous solvents. The reaction may be conducted at a temperature in the range of from about 25°C. to the reflux temperature of the particular solvent employed. The reaction with the alkylating or arylating agent is generally complete in about 10 to 60 minutes.

Still another method for preparing a 2,2-disubstituted-6-lower alkoxy-1,3-indanedione (IIIa, above) is effected by treating the corresponding 2-substituted compound V with a suitable arylating agent such as diaryliodonium halide, e.g. diphenyliodonium chloride or di-(substituted phenyl)iodonium halide, e.g. ditolyliodonium chloride or di-(p-chlorophenyl)iodonium chloride. Likewise, dithienyl iodonium halide is used to introduce the thienyl group into the 2-position of a 2-substituted indandione.

This reaction is conducted by first treating the 2-substituted compound V with a suitable base for example an alkali metal hydride such as sodium hydride and the like, an alkali metal alkoxide for example sodium ethoxide, potassium tertiary butoxide and the like; or an alkali metal amide such as sodium amide, lithium amide and the like. The resulting carbanion is then treated with the arylating agent. Any solvent which is inert or substantially inert to the reactants employed may be used; suitable solvents include for example 1,2-dimethoxyethane, tertiary butanol, benzene, dimethylformamide and the like. The reaction may be conducted at a temperature in the range of from about 25°–150°C. The following equation illustrates this process:

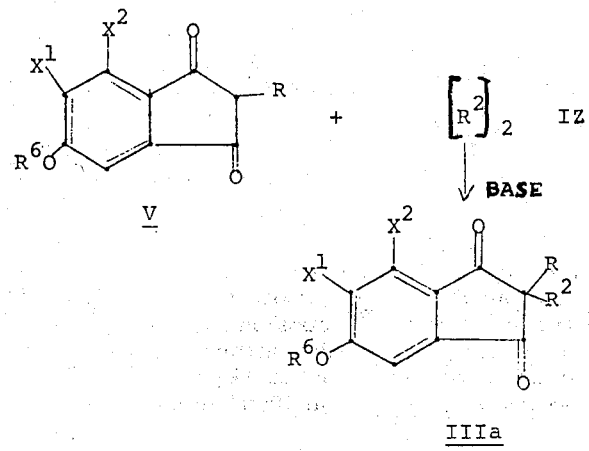

wherein all substituents are as defined above and $R^6$ is lower alkyl.

The 2-monosubstituted-6-lower alkoxy-1,3-indanediones (V, supra) are prepared by reacting a phthalate ester (VI, infra) with a ketone, $(RCH_2)_2C=O$ in an inert solvent such as benzene, toluene, xylene and the like in the presence of a base such as sodium hydride, potassium tert-butoxide and the like at a temperature of from 50°C. to 150°C. but preferably at the refluxing temperature of the solvent employed. The following equation illustrates this process.

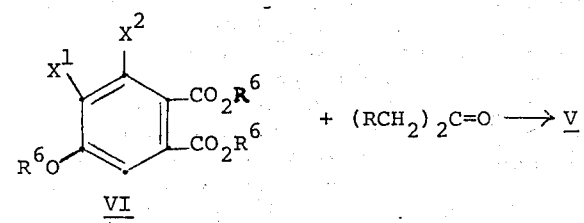

wherein R, $R^6$, $X^1$ and $X^2$ are as defined above.

The phthalic acids (VIa, infra) which are esterified by methods well known to those skilled in the art to give the phthalate esters (VI, supra), are prepared by the oxidation of a 2-substituted-5-lower alkoxy-1-indanone (VII, infra) with an oxidizing agent such as potassium permanganate, sodium dichromate or chromic acid and the like in a suitable solvent such as water or acetone and the like. The reaction is conducted at from 25°C. to 100°C. but preferably at the reflux temperature of the solvent employed. The following equation illustrates this process:

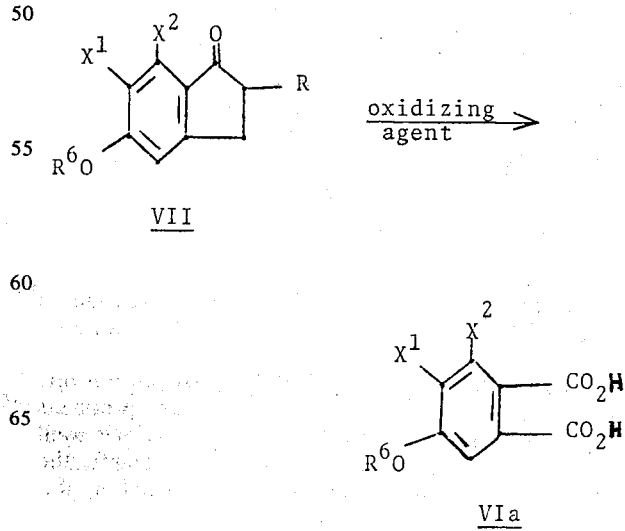

wherein R, $R^6$, $X^1$ and $X^2$ are as defined above with the exception that $X^1$ and $X^2$ are limited to halogen.

The 2-substituted-5-lower alkoxy-1-indanones (VII, supra) are prepared by alkylating a 2-substituted-5-hydroxy-1-indanone (VIII, infra) with an alkylating agent, $R^6Z$, in the presence of a base such as sodium carbonate, potassium carbonate, sodium hydroxide and the like in the presence of an inert solvent such as ethanol, dimethylformamide, acetone and the like at temperatures of from 25°C. to the reflux temperature of the solvent employed.

The following equation illustrates this process:

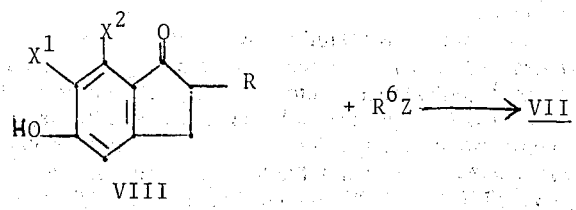

Also included within this invention are the enantiomers which can be prepared by resolution of the diastereomers by fractional crystallization of salts derived from optically active amines followed by regeneration (by acidification) of the resolved acid. Alternate methods of resolution of diastereomeric acids are known to anyone skilled in the art.

Included within the scope of this invention are the ester and amide derivatives of the instant products which are prepared by conventional methods well known to those skilled in the art. Thus, for example, the ester derivative may be prepared by the reaction of a 2-substituted or a [1,3-dioxo-2,2-disubstituted-indanyloxy(or thio)]alkanoic acid of this invention with an alcohol, for example, with a lower alkanol. The amide derivatives may be prepared by converting a 2-substituted and [1,3-dioxo-2,2-disubstituted-indanyloxy(or thio)]anlanoic acid to its corresponding acid chloride by treatment with thionyl chloride followed by treating said acid chloride with ammonia, an appropriate mono-lower alkyl amine, di-lower alkyl amine or a hetero amine, such as piperidine, morpholine and the like, to produce the corresponding amide compound. These and other equivalent methods for the preparation of the ester and amide derivatives of the instant products will be apparent to one having ordinary skill in the art and to the extent that said derivatives are both non-toxic and physiologically acceptable to the body system, said derivatives are the functional equivalent of the corresponding [1,3-dioxo-2-substituted and 2,2-disubstituted-indanyloxy(or thio)]alkanoic acids.

In addition to the salts, esters and amides being functionally equivalent to the carboxylic products those compounds wherein the carboxylic acid is replaced by a 5-tetrazolyl radical are also functionally equivalent to the carboxylic acids. These tetrazole analogs are prepared as depicted in the following equation:

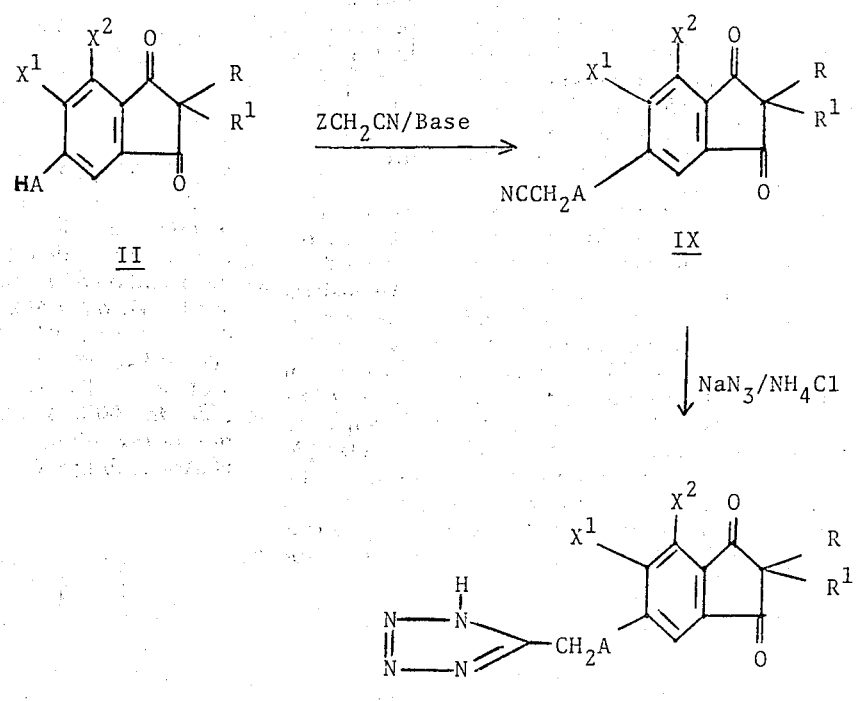

wherein A, R, $R^1$, $X^1$, $X^2$ and Z are as defined above.

The 2-substituted-6-hydroxy-indan-1,3-dione (II) is treated with a haloacetonitrile such as chloroacetonitrile, bromoacetonitrile or iodoacetonitrile in the presence of a base such as potassium carbonate and the like in a suitable solvent such as acetone, dimethylformamide, dimethoxyethane and the like at a temperature in the range of from 25° to 100°C. to afford the corresponding nitrile (IX, supra) which, upon treatment with sodium azide and ammonium chloride in dimethylformamide at a temperature in the range of from 25° to 100°C., affords the 5-(1,3-dioxo-2-substituted-6-indanyloxymethyl)tetrazole (X, supra).

The following examples describe the preparation of specific compounds of this invention and are meant to be illustrative only and not limiting to the scope of this invention.

EXAMPLE 1

(1,3-Dioxo-2,2-diethyl-4,5-dimethyl-6-indanyloxy)-acetic acid

Step A:

2,2-Diethyl-4,5-dimethyl-6-methoxy-indan-1,3-dione

A stirred mixture of 2,3-dimethylanisole (6.8 g., 0.05 mole) and 2,2-diethylmalonyl chloride (10 g., 0.051 mole) in hexane (75ml.) is cooled to 0°C. and treated with aluminum chloride (13.5 g., 0.11 mole) in several portions over a 15 minute period. The reaction is heated at reflux for 2 hours, the hexane is distilled at reduced pressure, the product treated with cold 1N-hydrochloric acid, extracted into ether, washed with water, 5% sodium hydroxide, water then dried over magnesium sulfate. Evaporation of the ether at reduced pressure affords 6.3 g. of 2,2-diethyl-4,5-dimethyl-6-methoxy-indan-1,3-dione which melts at 80°–81°C. after recrystallization from petroleum ether.

Elemental analysis for $C_{16}H_{20}O_3$:
 Calc.: C, 73.82; H, 7.74;
 Found: C, 74.16; H, 7.79.

Step B:

2,2-Diethyl-4,5-dimethyl-6-hydroxy-indan-1,3-dione

A mixture of 2,2-diethyl-4,5-dimethyl-6-methoxy-indan-1,3-dione (5.5 g., 0.021 mole) and pyridine hydrochloride (50 g.) is heated at 180°C. for six hours then poured into water (1 l.) affording 4.0 g. of 2,2-diethyl-4,5-dimethyl-6-hydroxy-indan-1,3-dione which melts at 141°–142°C. after recrystallization from methanol-water.

Elemental analysis for $C_{15}H_{18}O_3$:
 Calc.: C, 73.15; H, 7.37;
 Found: C, 73.65; H, 7.64.

Step C:

(1,3-Dioxo-2,2-diethyl-4,5-dimethyl-6-indanyloxy)-acetic acid

A stirred mixture of 2,2-diethyl-4,5-dimethyl-6-hydroxy-indan-1,3-dione (3.5 g., 0.014 mole), ethyl bromoacetate (2.7 g., 0.016 mole) and potassium carbonate (2.2 g., 0.016 mole) in dimethylformamide (20 ml.) is heated at 65°C. for 2 hours, treated with methanol (40 ml.) and potassium hydroxide (1.1 g., 0.02 mole) refluxed for ½ hour then poured into dilute hydrochloric acid (500 ml.) affording 4.2 g. of (1,3-dioxo-2,2-diethyl-4,5-dimethyl-6-indanyloxy)-acetic acid which melts at 134°–136°C. after recrystallization from acetic acid-water.

Elemental analysis for $C_{17}H_{20}O_5$:
 Calc.: C, 67.09; H, 6.62;
 Found: C, 67.44; H, 6.66.

EXAMPLE 2

(1,3-Dioxo-2,2-diethyl-4,5-dimethyl-6-indanyloxy)-acetic acid

A stirred solution of (2,3-dimethylphenoxy)acetic acid (4.5 g., 0.025 mole) and 2,2-diethylmalonyl chloride (5.0 g., 0.0255 mole) in methylene chloride (200 ml.) is cooled to 0°C. and treated in portions with aluminum chloride (10.7 g., 0.08 mole) during a 15 minute period. The reaction is stirred 18 hours at 25°C. then one hour at reflux, cooled and poured into water (500 ml.) containing hydrochloric acid (25 ml.). Evaporation of the methylene chloride affords 6.1 g. of (1,3-dioxo-2,2-diethyl-4,5-dimethyl-6-indanyloxy)-acetic acid which melts at 134°–136°C.

EXAMPLE 3

(1,3-Dioxo-2-ethyl-4,5-dimethyl-6-indanyloxy)acetic acid

A solution of methyl (2,3-dimethylphenoxy)acetate (3.0 g., 0.0155 mole) and 2-ethylmalonyl chloride (2.7 g., 0.016 mole) in methylene chloride (200 ml.) is cooled to 0°C. then treated with aluminum chloride (6.6 g., 0.05 mole) in several portions during a 15 minute period. The reaction is stirred for 2 hours at 0°C., 18 hours at 25°C. then at reflux for 6 hours, cooled and poured into cold 1 N-hydrochloric acid (500 ml.), the organic layer is washed with water, saturated aqueous sodium chloride, dried over magnesium sulfate, then the solvent evaporated at reduced pressure. The crude methyl ester is hydrolyzed by treatment with potassium hydroxide (0.34 g., 0.005 mole) and methanol (20 ml.) at reflux for ½ hour, cooled and acidified with aqueous hydrochloric acid affording (1,3-dioxo-2-ethyl-4,5-dimethyl-6-indanyloxy)acetic acid which melts at 187°–193°C. after recrystallization from acid-water.

Elemental analysis for $C_{15}H_{16}O_5$:
 Calc.: C, 65.21; H, 5.84;
 Found: C, 65.09; H, 5.66.

EXAMPLE 4

(1,3-Dioxo-2-cyclopentyl-2,5-dimethyl-4-chloro-6-indanyloxy)-acetic acid

Step A: 2-Cyclopentyl-2-methylmalonyl chloride

Phosphorus pentachloride (60.4 g., 0.29 mole) is added in portions to 2-cyclopentyl-2-methylmalonic acid (26.6 g., 0.143 mole) causing an exothermic reaction. The clear, hot solution is then heated at 95°C. for three hours and distilled affording 29 g. (91%) of 2-cyclopentyl-2-methylmalonyl chloride which distills at 135°–6°/30 mm.

Step B:

2-Cyclopentyl-2,5-dimethyl-4-chloro6-methoxy-indan-1,3-dione

2-Cyclopentyl-2,5-dimethyl-4-chloro-6-methoxy-indan-1,3-dione is prepared following substantially the same procedure described in Example 1, Step A using the following substances:

| | |
|---|---|
| 2-Methyl-3-chloroanisole | 7 g. (0.045 mole) |
| 2-Cyclopentyl-2-methylmalonyl chloride | 11.2 g. (0.05 mole) |
| Methylene chloride | 400 ml. |
| Aluminum chloride | 13.5 g. (0.10 mole) |

The above procedure gives 9 g. of crude 2-cyclopentyl-2,5-dimethyl-4-chloro-6-methoxy-indan-1,3-dione which is used in the next step without further purification.

Step C:
2-Cyclopentyl-2,5-dimethyl-4-chloro-6-hydroxy-indan-1,3-dione

2-Cyclopentyl-2,5-dimethyl-4-chloro-6-hydroxyindan-1,3-dione is prepared following substantially the same procedure described in Example 1, Step B using the following substances:

| | |
|---|---|
| 2-Cyclopentyl-2,5-dimethyl-4-chloro-6-methoxy-indan-1,3-dione | 2.53 g. (0.00825 mole) |
| Pyridine hydrochloride | 20 g. |

The above procedure gives 2.3 g. of 2-cyclopentyl-2,5-dimethyl-4-chloro-6-hydroxy-indan-1,3-dione which after recrystallization from acetic acid-water melts at 221°–2°C.

Elemental analysis for $C_{16}H_{17}ClO_3$:
Calc.: C, 65.64; H, 5.85;
Found: C, 65.74; H, 5.85.

Step D:
(1,3-Dioxo-2-cyclopentyl-2,5-dimethyl-4-chloro-6-indanyloxy)acetic acid (1,3-Dioxo-2-cyclopentyl-2,5-dimethyl-4-chloro-6-indanyloxy)acetic acid is prepared following substantially the same procedure described in Example 1, Step C using the following substances:

| | |
|---|---|
| 2-Cyclopentyl-2,5-dimethyl-4-chloro-6-hydroxy-indan-1,3-dione | 2 g. (6.85 m mole) |
| Ethyl bromoacetate | 1.25 g. (7.5 m mole) |
| Potassium carbonate | 1.04 g. (7.5 m mole) |
| Dimethylformamide | 20 ml. |
| Methanol | 40 ml. |
| Potassium hydroxide | 0.5 g. (9.0 m mole) |

The above procedure gives 2.2 g. of (1,3;-dioxo-2-cyclopentyl-2,5-dimethyl-4-chloro-6-indanyloxy)acetic acid which after recrystallization from acetic acid-water melts at 178°–80°C.

Elemental analysis for $C_{18}H_{19}ClO_5$:
Calc.: C, 61.63; H, 5.46;
Found: C, 61.69; H, 5.75.

EXAMPLE 5

[1',3'-Dioxo-4'-chloro-5'-methylspiro(cyclopentane-1,2'-indan)-6'-yloxy]acetic acid Step A: Cyclopentane-1,1-dicarbonyl chloride Phosphorous pentachloride (73 g., 0.35 mole) is added in portions to cyclopentane-1,1-dicarboxylic acid (27 g., 0.17 mole) causing an exothermic reaction. The clear hot solution is heated at 95°C. for 3 hours then distilled affording 23 g. of cyclopentane-1,1-dicarbonyl chloride which distills at 105°–115°C./35 mm.

Step B: Methyl [1',3'-dioxo-4'-chloro-5'-methylspiro(cyclopentane-1,2'-indan)-6'-yloxy]-acetate A stirred solution of methyl (2-methyl-3-chlorophenoxy)acetate (3.7 g., 0.0172 mole) and cyclopentane-1,1-dicarbonyl chloride (3.5 g., 0.018 mole) in methylene chloride (200 ml.) is cooled to 0°C. and treated with aluminum chloride (7.2 g., 0.054 mole) in several portions during a 15 minute period. The reaction is stirred at 25°C. for 18 hours then at reflux for 5 hours, cooled and poured into 1N-hydrochloric acid. Evaporation of the methylene chloride at reduced pressure affords methyl [1', 3'-dioxo-4'-chloro-5'-methylspiro(cyclopentane-1,2'-indan)-6'-yloxy]acetate which melts at 152°–153.5°C. after recrystallization from ethanol-water. Elemental analysis for $C_{17}H_{17}ClO_5$:
Calc.: C, 60.63; H, 5.09; Found: C, 60.51; H, 5.24.

Step C:
[1',3'-Dioxo-4'-chloro-5'-methylspiro(cyclopentane-1,2'-indan)-6'-yloxy]acetic acid A mixture of methyl [1',3'-dioxo-4'-chloro-5'-methylspiro(cyclopentane-1,2'-indan)-6'-yloxy]acetate (3.5 g., 0.0104 mole) potassium hydroxide (0.67 g., 0.012 mole) and methanol (200 ml.) is refluxed for ½ hour, diluted with water (800 ml.) and acidified with hydrochloric acid affording 3.1 g. of [1',3'-dioxo-4'-chloro-5'-methylspiro(cyclopentane-1,2'-indan)-6'-yloxy]acetic acid which melts at 204°–5°C. after recrystallization from acetic acid-water.

Elemental analysis for $C_{16}H_{15}ClO_5$:
Calc.: C, 59.54; H, 4.68;
Found: C, 59.88; H, 4.74.

EXAMPLE 6

(1,3-Dioxo-2,2-diethyl-4-chloro-5-methyl-6-indanyloxy)acetic acid

Step A: Methyl (1,3-dioxo-4-chloro-2,2-diethyl-5-methyl-6-indanyloxy)acetate

Methyl (1,3-dioxo-2,2-diethyl-4-chloro-5-methyl-6-indanyloxy)acetate is prepared following substantially the same procedure described in Example 5, Step B using the following substances:

| | |
|---|---|
| Methyl (2-methyl-3-chlorophenoxy)acetate | 5.13 g. (0.025 mole) |
| 2,2-Diethylmalonyl chloride | 5 g. (0.0255 mole) |
| Methylene chloride | 200 ml. |
| Aluminum chloride | 10.7 g. (0.08 mole) |

The above procedure gives 8 g. of methyl (1,3-dioxo-2,2-diethyl-4-chloro-5-methyl-6-indanyloxy)acetate which after recrystallization from methanol-water melts at 141°–142.5°C.

Elemental analysis for $C_{17}H_{19}ClO_5$:
Calc.: C, 60.27; H, 5.65;
Found: C, 60.22; H, 5.68.

Step B:
(1,3-Dioxo-2,2-diethyl-4-chloro-5-methyl-6-indanyloxy)acetic acid (1,3-Dioxo-2,2-diethyl-4-chloro-5-methyl-6-indanyloxy)acetic acid is prepared following substantially the same procedure described in Example 5, Step C using the following substances:

| | |
|---|---|
| Methyl (1,3-dioxo-2,2-diethyl-4-chloro-5-methyl-6-indanyloxy)acetate | 5 g., (0.0148 mole) |
| Potassium hydroxide | 0.98 g., (0.0175 mole) |
| Methanol | 200 ml. |

The above procedure gives 4.4 g. of (1,3-dioxo-2,2-diethyl-4-chloro-5-methyl-6-indanyloxy)acetic acid which after recrystallization from cetic acid-water melts at 167°–8.5°C.

Elemental analysis for $C_{16}H_{17}ClO_5$:
Calc.: C, 59.17; H, 5.28;
Found: C, 59.55; H, 5.18.

EXAMPLE 7

(1,3-Dioxo-2-ethyl-2-methyl-4,5-dichloro-6-indanyloxy)acetic acid

Step A: 2-Ethyl-5-methoxy-6,7-dichloro-1-indanone

A stirred mixture of 2-ethyl-5-hydroxy-6,7-dichloro-1-indanone (18.3 g., 0.075 mole), potassium carbonate (23 g.) and methyl iodide (15 ml.) in DMF (100 ml.) is warmed at 55°C. for 2 hours and poured into water (300 ml.). The 2-ethyl-5-methoxy-6,7-dichloro-1-indanone which separates (18 g.) melts at 146°–147°C. after recrystallization from butyl chloride.

Elemental analysis for $C_{12}H_{12}Cl_2O_2$:
Calc.: C, 55.62; H, 4.67;
Found: C, 55.54; H, 4.55.

Step B: 3,4-Dichloro-5-methoxyphthalic acid

2-Ethyl-5-methoxy-6,7-dichloro-1-indanone (4 g.) is suspended in 200 ml. of water containing 1 ml. of 20% sodium hydroxide. The mixture is heated to boiling and potassium permanganate 18 g. is added portionwise over a 4 hour period in such a manner that each time the purple color disappears an additional portion is added. A few drops of methanol are added to destroy the excess permanganate and the manganese oxide is removed by filtration.

The colorless filtrate is acidified with 6N-hydrochloric acid and evaporated to dryness under reduced pressure. The solid residue is extracted with boiling acetone and the extract is evaporated to dryness. The residue (2.57 g.) is suspended in 6N hydrochloric acid (125 ml) and the mixture is boiled for 10 min., cooled and the 3,4-dichloro-5-methoxyphthalic acid is collected. On heating the product in a capillary m.p. tube, it evolves a gas at ca. 210°C. (formation of the anhydride), resolidifies and melts at 218°–220°C.

Step C: Dimethyl (3,4-dichloro-5-methoxy)phthalate

Methyl iodide (20 g., 0.2 mole) is added dropwise during a two hour period to a stirred mixture of 3,4-dichloro-5-methoxy phthalic acid (17.5 g., 0.07 mole) and potassium carbonate (21 g., 0.15 mole) in dimethylformamide (175 ml.) at a temperature of 55°–60°C. The reaction is heated at 55°–60°C. for 4 additional hours then poured into water (800 ml.) affording 14.5 g. of dimethyl (3,4-dichloro-5-methoxy)phthalate which melts at 109°–111°C. after recrystallization from ether-hexane.

Elemental analysis for $C_{11}H_{10}Cl_2O_5$:
Calc.: C, 45.07; H, 3.44; Cl, 24.19;
Found: C, 45.14; H, 3.35; Cl, 24.28.

Step D: 2-Ethyl-4,5-dichloro-6-methoxyindan-1,3-dione

To a dispersion of sodium hydride (50% in mineral oil, 0.32 g., 6.6 m moles) in dry toluene (20 ml.) is added dimethyl (3,4-dichloro-5-methoxy)phthalate (1.9 g., 6.5 m moles) and 4-heptanone (0.75 g., 6.6 m mole). The reaction is refluxed for 18 hours, cooled and the sodium salt of the product collected and rinsed with benzene. The solid is then dissolved in water and acidified with dilute hydrochloric acid affording 0.9% of 2-ethyl-4,5-dichloro-6-methoxyindan-1,3-dione which melts at 153°–4°C. after recrystallization from methanol-water.

Elemental analysis for $C_{12}H_{10}Cl_2O_3$:
Calc.: C, 52.77; H, 3.69; Cl, 25.96;
Found: C, 52.50; H, 3.61; Cl, 25.94.

Step E: 2-Ethyl-2-methyl-4,5-dichloro-6-methoxyindan-1,3-dione

A stirred solution of 2-ethyl-4,5-dichloro-6-methoxyindan-1,3-dione (1.3 g.) in dimethylformamide (15 ml.) is treated with potassium carbonate (1.26 g.) and metyl iodide. After 15 minutes, the reaction is poured into water (75 ml.) affording 1.3 g. of 2-ethyl-2-methyl-4,5-dichloro-6-methoxyindan-1,3-dione which melts at 157°C. after recrystallization from ethanol.

Elemental analysis for $C_{13}H_{12}Cl_2O_3$:
Calc.: C, 54.38; H, 4.21;
Found: C, 54.68; H, 4.28.

Step F: 2-Ethyl-2-methyl-4,5-dichloro-6-hydroxyindan-1,3-dione

2-Ethyl-2-methyl-4,5-dichloro-6-hydroxyindan-1,3-dione is prepared following substantially the same procedure described in Example 1, Step B using the following substances:

| | |
|---|---|
| 2-Ethyl-2-methyl-4,5-dichloro-6-methoxyindan-1,3-dione | 1.1 g. |
| Pyridine hydrochloride | 10 g. |

The above procedure gives 1.0 g. of 2-ethyl-2-methyl-4,5-dichloro-6-hydroxyindan-1,3-dione which after recrystallization from acetic acid melts at 246°C.

Elemental analysis for $C_{12}H_{10}Cl_2O_3$:
Calc.: C, 52.77; H, 3.69;
Found: C, 52.87; H, 3.73.

Step G: (1,3-Dioxo-2-ethyl-2-methyl-4,5-dichloro-6-indanyloxy)acetic acid (1,3-Dioxo-2-ethyl-2-methyl-4,5-dichloro-6-indanyloxy)acetic acid is prepared following substantially the same procedure described in Example 1, Step C using the following substances:

| | |
|---|---|
| 2-Ethyl-2-methyl-4,5-dichloro-6-hydroxyindan-1,3-dione | 690 mg. |
| Potassium carbonate | 925 mg. |
| Ethyl bromoacetate | 1.12 g. |
| Dimethylformamide | 8 ml. |
| Water | 8 ml. |
| 10N sodium hydroxide | 0.7 ml. |

The above procedure gives 780 mg. of (1,3-dioxo-2-ethyl-2-methyl-4,5-dichloro-6-indanyloxy)acetic acid which after recrystallization from nitromethane melts at 214°C.

Elemental analysis for $C_{14}H_{12}Cl_2O_5$:
Calc.: C, 50.77; H, 3.65;
Found: C, 50.62; H, 3.70.

EXAMPLE 8

(1,3-Dioxo-2-ethyl-2-phenyl-4,5-dichloro-6-indanyloxy)acetic acid

Step A:
2-Ethyl-2-phenyl-4,5-dichloro-6-methoxyindan-1,3-dione

Potassium tert-butoxide (8.4 g.) dissolved in tert-butanol (300 ml.) is added to a refluxing solution of 2-ethyl-4,5-dichloro-6-methoxyindan-1,3-dione (1.3 g) in tert-butanol (400 ml.)-benzene (200 ml.) and refluxing is continued for 15 min., then diphenyliodonium chloride (19.0 g.) is added and refluxing is continued for an additional 2 hours. The reaction mixture is cooled to 25°, 300 ml. water added, and the mixture concentrated to dryness in vacuo to give 2-ethyl-2-phenyl-4,5-dichloro-6-methoxyindan-1,3-dione.

Step B:
2-Ethyl-2-phenyl-4,5-dichloro-6-hydroxyindan-1,3-dione

By the process of Example 7, Step F, but substituting for the 2-ethyl-2-methyl-4,5-dichloro-6-methoxyindan-1,3-dione used therein, an equivalent amount of 2-ethyl-2-phenyl-4,5-dichloro-6-methoxyindan-1,3-dione there is obtained 2-ethyl-2-phenyl-4,5-dichloro-6-hydroxyindan-1,3-dione.

Step C:
(1,3-Dioxo-2-ethyl-2-phenyl-4,5-dichloro-6-indanyloxy)acetic acid

By the process of Example 7, Step G, but substituting for the 2-ethyl-2-methyl-4,5-dichloro-6-hydroxyindan-1,3-dione used therein, an equivalent amount of 2-ethyl-2-phenyl-4,5-dichloro-6-hydroxyindan-1,3-dione, there is obtained (1,3-dioxo-2-ethyl-2-phenyl-4,5-dichloro-6-indanyloxy)acetic acid.

EXAMPLE 9

5-[1',3'-Dioxo-4'-chloro-5'-methylspiro(cyclopentane-1,2'-indan)-6'-yloxymethyl]tetrazole

Step A:
4'-Chloro-5'-methyl-6'-methoxyspiro(cyclopentane-1,2'-indan)-1',3'-dione 4'-Chloro-5'-methyl-6'-methoxyspiro(cyclopentane-1,2'-indan)-1',3'-dione is prepared following substantially the same procedure described in Example 1, Step A using the following substances:

| | | |
|---|---|---|
| 2-Methyl-3-chloroanisole | 7.8 g. | (0.05 mole) |
| Cyclopentane-1,1-dicarbonyl chloride | 10.7 g. | (0.055 mole) |
| Methylene chloride | 400 ml. | |
| Aluminum chloride | 14.7 g. | (0.11 mole) |

The above procedure gives 11 g. of 4'-chloro-5'-methyl-6'-methoxyspiro(cyclopentane-1,2'-indan)-1',3'-dione which after recrystallization from ethanol-water melts at 156°–7°C.

Elemental analysis for $C_{15}H_{15}ClO_3$:
Calc.: C, 64.64; H, 5.42;
Found: C, 65.12; H, 5.47.

Step B:
4'-Chloro-5'-methyl-6'-hydroxyspiro(cyclopentane-1,2'indan)-1',3'-dione 4'-Chloro-5'-methyl-6'-hydroxyspiro(cyclopentane-1,2'-indan)-1',3'-dione is prepared following substantially the same procedure described in Example 1 Step B using the following substances:

| | | |
|---|---|---|
| 4'-Chloro-5'-methyl-6'-methoxyspiro-(cyclopentane-1,2'-indan)-1,3'-dione | 10.5 g. | (0.0375 mole) |
| Pyridine hydrochloride | 75 g. | |

The above procedure gives 9.8 g. of 4'-chloro-5'-methyl-6'-hydroxyspiro(cyclopentane-1,2'-indan)-1',3'-dione which after recrystallization from acetic acid-water melts at 297°–8°C.

Elemental analysis for $C_{14}H_{13}ClO_3$:
Calc.: C, 63.52; H, 4.95;
Found: C, 63.47; H, 4.89.

Step C:
[1',3'-Dioxo-4'-chloro-5'-methylspiro(cyclopentane-1,2'-indan)-6'-yloxyl]acetonitrile A stirred mixture of 4'-chloro-5'-methyl-6'-hydroxyspiro(cyclopentane-1,2'-indan)-1',3'-dione (9.3 g., 0.035 mole), chloroacetonitrile (2.83 g., 0.0375 mole), potassium carbonate (5.2 g., 0.0375 mole) and potassium iodide (6.2 g., 0.0375 mole) in dimethylformamide (100 ml.) is heated at 65°C. for 2½ hours, cooled, then poured into water (1.5 l.) affording 10.7 g. of [1',3'-dioxo-4'-chloro-5'-methylspiro(cyclopentane-1,2'-indan)-6'-yloxylacetonitrile which melts at 137°–9°C. after recrystallization from ethanol-water.

Elemental analysis for $C_{16}H_{14}ClNO_3$:
Calc.: C, 63.27; H, 4.65; N, 4.61;
Found: C, 63.54; H, 4.74; N, 4.63.

Step D:
5-[1',3'-Dioxo-4'-chloro-5'-methylspiro(cyclopentane-1,2'-indan)-6'-yloxymethyl]tetrazole A stirred mixture of [1',3'-dioxo-4'-chloro-5'-methylspiro(cyclopentane-1,2'-indan)-6'-yloxy]acetonitrile (9.0 g., 0.03 mole), sodium azide (3.9 g., 0.06 mole) and ammonium chloride (3.2 g., 0.06 mole) in dimethylformamide (150 ml.) is heated at 95°C. for 2 hours then cooled and poured into dilute aqueous hydrochloric acid affording 9.9 g. of 5-[1',3'-dioxo-4'-chloro-5'-methylspiro(cyclopentane-1,2'-indan)-6'-yloxymethyl]tetrazole which melts at 211°–212'C. after recrystallization from acetic acid-water.

Elemental analysis for $C_{16}H_{15}ClN_4O_3$:
Calc.: C, 55.42; H, 4.36; N, 16.16;
Found: C, 55.38; H, 4.29; N, 16.37.

EXAMPLE 10

(1,3-Dioxo-2-methyl-2-phenyl-4,5-dichloro-6-indanyloxy)-acetic acid

Step A:
2-Methyl-4,5-dichloro-6-methoxyindan-1,3-dione

To a dispersion of sodium hydride (50% in mineral oil, 3.2 g., 66 m moles) in dry toluene (200 ml.) is added dimethyl (3,4-dichloro-5-methoxy)phthalate (19 g., 65 m moles), prepared by the method described in Example 7, Step A, B and C, and 3-pentanone (5.7 g., 66 m mole). The reaction is refluxed for 18 hours, cooled and the sodium salt of the product collected and rinsed with benzene. The solid is then dissolved in water and acidified with dilute hydrochloric acid affording 2-methyl-4,5-dichloro-6-methoxyindan-1,3-dione.

Step B:
2-Methyl-2-phenyl-4,5-dichloro-6-methoxy-indan-1,3-dione

Potassium tert-butoxide (8.42 g., 0.075 mole) dissolved in tert-butanol (300 ml.) is added to a refluxing solution of 2-methyl-6-methoxy-4,5-dichloroindan-1,3-dione (12.95 g., 0.05 mole), refluxing is continued for 2 hrs., then a suspension of diphenyliodonium chloride (19.0 g., 0.06 mole) in tert-butanol (1 l.) is added and refluxing is continued for 2 hrs. The reaction mixture is cooled to 25°C., 300 ml. water added, and the mixture concentrated to dryness in vacuo to give 2-methyl-2-phenyl-4,5-dichloro-6-methoxyindan-1,3-dione.

Step C:
2-Methyl-2-phenyl-4,5-dichloro-6-hydroxyindan-1,3-dione

A stirred mixture of 2-methyl-2-phenyl-4,5-dichloro-6-methoxyindan-1,3-dione (5.01 g., 0.015 mole) and pyridine hydrochloride (50 g.) is heated at 175°C. for 1 hour, then poured into water (500 ml.) to give 2-methyl-2-phenyl-4,5-dichloro-6-hydroxyindan-1,3-dione.

Step D:
(1,3-Dioxo-2-methyl-2-phenyl-4,5-dichloro-6-indanyloxy)acetic acid A stirred mixture of 2-methyl-2-phenyl-4,5-dichloro-6-hydroxyindan-1,3-dione (2.14 g., 0.0067 mole), potassium carbonate (1.85 g., 0.0134 mole) and ethyl bromoacetate (2.32 g., 0.0134 mole) in dimethylformamide (30 ml.) is warmed at 55°–60°C. for 3 hours, then treated with potassium hydroxide (0.97 g., 0.0147 mole) dissolved in a minimum amount of water in methanol (30 ml.) and heated on a steam bath for 2½ hrs. The reaction mixture is poured into water (500 ml.), acidified with 6 N hydrochloric acid and the precipitate collected after trituration with ether-petroleum ether and dried to give (1,3-dioxo-2-methyl-2-phenyl-4,5-dichloro-6-indanyloxy)acetic acid.

EXAMPLE 11

Preparation of
[1,3-Dioxo-2-(p-chlorophenyl)-2-methyl-4,5-dichloro-6-indanyloxy]acetic acid

Step A:
2-(p-Chlorophenyl)-2-methyl-4,5-dichloro-6-methoxyindan-1,3-dione Potassium tert-butoxide (2.81 g., 0.025 mole) dissolved in tert-butanol (150 ml.) is added to a refluxing solution of 2-methyl-4,5-dichloro-6-methoxyindan-1,3-dione (5.18 g., 0.02 mole) prepared as described in Example 10, Step A, in tert-butanol (100 ml.)-benzene (200 ml.), refluxing is continued for 3 hrs., then 4,4'-dichlorodiphenyliodonium chloride (11.55 g., 0.03 mole) is added and refluxing is continued for 2 hrs. The reaction mixture is cooled to 25°C., 100 ml. water added, and the mixture concentrated to dryness in vacuo to give 2-(p-chlorophenyl)-2-methyl-4,5-dichloro-6-methoxyindan-1,3-dione.

Step B:
2-(p-Chlorophenyl)-2-methyl-4,5-dichloro-6-hydroxyindan-1,3-dione A stirred mixture of 2-(p-chlorophenyl)-2-methyl-4,5-dichloro-6-methoxyindan-1,3-dione (4.42 g., 0.012 mole) and pyridine hydrochloride (40 g.) is heated at 180°C. for 1 hour, then poured into water (500 ml.). The 2-(p-chlorophenyl)-2-methyl-4,5-dichloro-6-hydroxyindan-1,3-dione which separates is filtered and dried.

Step C:
[1,3-Dioxo-2-(p-chlorophenyl)-2-methyl-4,5-dichloro-6-indanyloxy]acetic acid A stirred mixture of 2-(p-chlorophenyl)-2-methyl-4,5-dichloro-6-hydroxyindan-1,3-dione (3.06 g., 0.00863 mole), potassium carbonate (2.26 g., 0.0163 mole) and ethylbromoacetate (2.72 g., 0.0163 mole) in dimethylformamide (50 ml.) is warmed at 55°–60°C. for two hours, then treated with water (50 ml.)-10N sodium hydroxide solution (2.5 ml., 0.025 mole) and heated at 80°C. for 1 hour. The reaction mixture is added slowly to water (500 ml.)-12N hydrochloric acid (10 ml.) to precipitate [1,3-dioxo-2-(p-chlorophenyl)-2-methyl-4,5-dichloro-6-indanyloxy]acetic acid.

EXAMPLE 12

[1,3-Dioxo-2-methyl-2-(2-thienyl)-4,5-dichloro-6-indanyloxy] acetic acids

Step A:
2-Methyl-2-(2-thienyl)-4,5-dichloro-6-methoxyindan-1,3-dione

Potassium tert-butoxide (5.06 g., 0.045 mole) dissolved in tert-butanol (100 ml.) is added to a refluxing solution of 2-methyl-4,5-dichloro-6-methoxyindan-1,3-dione (7.8 g., 0.03 mole), prepared by the method described in Example 10, Step A, in tert-butanol (150 ml.)-benzene (150 ml.). The mixture is cooled slightly and solid 2,2'-dithienyliodonium chloride (16.5 g., 0.05 mole) is added in one portion. Heating at reflux is continued for 2 hrs. The reaction mixture is cooled to 25°C., 100 ml. of water is added, and the mixture concentrated to dryness in vacuo to give 2-methyl-2-(2-thienyl(-4,5-dichloro-6-methoxyindan-1,3-dione.

Step B:
2-Methyl-2-(2-thienyl)-4,5-dichloro-6-hydroxyindan-1,3-dione.

A stirred mixture of 2-methyl-2-(2-thienyl)-4,5-dichloro-6-methoxyindan-1,3-dione (3.81 g., 0.0112 mole) and pyridine hydrochloride (36 g.) is heated at 175°C. for one half hour, then poured into crushed ice-water (500 ml.) to give 2-methyl-2-(2-thienyl)-4,5-dichloro-6-hydroxyindan-1,3-dione.

Step C:
[1,3-Dioxo-2-methyl-2-(2-thienyl)-4,5-dichloro-6-indanyloxy]acetic acid A stirred mixture of 2-methyl-2-(2-thienyl)-4,5-dichloro-6-hydroxyindan-1,3-dione (3.26 g., 0.01 mole), potassium carbonate (2.77 g., 0.02 mole) and ethyl bromoacetate (3.34 g., 0.02 mole) in dimethylformamide (40 ml.) is warmed at 55°–60°C. for 2 hrs., then treated with water (40 ml.) and 10N sodium hydroxide solution (4 ml., 0.04 mole) and heated at 100°C. for 1 hr. The reaction mixture is added slowly to crushed ice-water (700 ml.)-12N hydrochloric acid (10 ml.) to precipitate [1,3-dioxo-2-methyl-2-(2-thienyl)-4,5-dichloro-6-indanyloxy]acetic acid.

The novel compounds of this invention are diuretic and saluretic agents. In addition, these compounds are also able to maintain the uric acid concentration in the blood at pretreatment levels or even cause a decrease in uric acid concentration. The compounds of this invention can be administered to patients both animal and human) in a wide variety of therapeutic dosages in conventional vehicles as, for example, by oral administration in the form of a tablet or by intravenous injection. Also, the daily dosage of the products may be varied over a wide range as, for example, in the form of scored tablets containing 5, 10, 25, 50, 100, 150, 250, 500 and 1000 milligrams of the active ingredient for the symptomatic adjustment of the dosage to the patient to be treated. These dosages are well below the toxic or lethal dose of the products.

A suitable unit dosage form of the products of this invention can be administered by mixing 50 milligrams of a [1,3-dioxo-2-substituted or 2,2-disubstituted-indanyloxy (or thio)]alkanoic acid (I) or a suitable salt, ester or amide derivative thereof, with 149. mg. of lactose and 1 mg. of magnesium stearate and placing the 200 mg. mixture into a No. 1 gelatin capsule. Similarly, by employing more of the active ingredient and less lactose, other dosage forms can be put up in No. 1 gelatin capsules and, should it be necessary to mix more than 200 mg. of ingredients together, larger capsules may be employed. Compressed tablets, pills, or other desired unit dosages can be prepared to incorporate the compounds of this invention by conventional methods, and if desired, can be made up as elixirs or as injectable solutions by methods well known to pharmacists. An effective amount of the drug is ordinarily supplied at a dosage level of from about 1 mg. to about 50 mg./kg. of body weight. Preferably the range is from about 1 mg. to 7 mg./kg. of body weight.

It is also within the scope of this invention to combine two or more of the compounds of this invention in a unit dosage form or to combine one or more of the compounds of this invention with other known diuretics and saluretics or with other desired therapeutic and/or nutritive agents in dosage unit form.

The following example is included to illustrate the preparation of a representative dosage form:

Dry-filled capsules containing 50 mg. of active ingredient per capsule

| | Per Capsule |
|---|---|
| (1,3-Dioxo-2-methyl-2-phenyl-4,5-dichloro-6-indanyloxy)-acetic acid | 50 mg. |
| Lactose | 149 mg. |
| Magnesium Stearate | 1 mg. |
| Capsule (Size No. 1) | 200 mg. |

The (1,3-dioxo-2-methyl-2-phenyl-4.5-dichloro-6-indanyloxy)acetic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other novel compounds of this invention.

It will be apparent from the foregoing description that the [1,3-dioxo-2-substituted and 2,2-disubstituted-indanyloxy(or thio)]alkanoic acid (I) of this invention constitute a valuable class of compounds which have not been prepared heretofore. One skilled in the art will also appreciate that the processes disclosed in the above examples are merely illustrative and are capable of a wide variation and modification without departing from the spirit of this invention.

What is claimed is:

1. A pharmaceutical composition useful in the treatment of edema and hypertension which also maintains uric acid at pretreatment levels or causes a decrease in uric acid in patients which comprises along with a pharmaceutically acceptable carrier 50 mg. to 500 mg. of a compound of the formula:

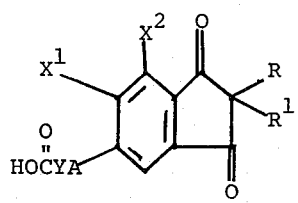

wherein
A is oxygen;
R is lower alkyl having from 1 to 5 carbon atoms, cycloalkyl, phenyl or substituted phenyl wherein the substituent is lower alkyl or halo,
$R^1$ is hydrogen, lower alkyl having 1 to 5 carbon atoms, lower alkenyl having 3 to 5 carbon atoms, lower alkynyl having from 3 to 5 carbon atoms, phenyl lower alkyl wherein lower alkyl has 1 to 3 carbon atoms, phenyl lower alkenyl wherein lower alkenyl has 2 to 5 carbon atoms, phenyl or substituted phenyl wherein the substituent is lower alkyl or halo;
$X^1$ is hydrogen, methyl or halo; and
$X^2$ is methyl or halo; and
Y is alkylene or haloalkylene containing a maximum of 4 carbon atoms, and
the racemic form, the enantiomers and the non-toxic, pharmacologically acceptable salt thereof.

2. A method for the treatment of edema and hypertension which comprises administering to a patient in need of said treatment a unitary dosage of from 50 mg. to 500 mg. of a compound of the formula:

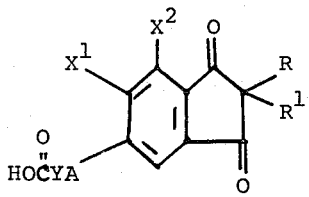

wherein
A is oxygen;
R is lower alkyl having from 1 to 5 carbon atoms, cycloalkyl, phenyl or substituted phenyl wherein the substituent is lower alkyl or halo;
$R^1$ is hydrogen, lower alkyl having 1 to 5 carbon atoms, lower alkenyl having 3 to 5 carbon atoms, lower alkynyl having from 3 to 5 carbon atoms, phenyl lower alkyl wherein lower alkyl has 1 to 3 carbon atoms, phenyl lower alkenyl wherein the lower alkenyl has 2 to 5 carbon atoms, phenyl or substituted phenyl wherein the substituent is lower alkyl or halo;

$X^1$ is hydrogen, methyl or halo; and $X^2$ is methyl or halo; and

Y is alkylene or haloalkylene containing a maximum of 4 carbon atoms, and the racemic form, the enantiomers and the non-toxic, pharmacologically acceptable salt thereof.

3. The pharmaceutical composition of claim 1 wherein the compound is (1,3-dioxo-2-cyclopentyl, 2,5-dimethyl-4-chloro-6-indanyloxy)acetic acid.

4. The method of treatment of claim 2 wherein the compound to be administered is (1,3-dioxo-2-cyclopentyl-2,5-dimethyl-4-chloro-6-indanyloxy)acetic acid.

* * * * *